(12) United States Patent
Jian et al.

(10) Patent No.: US 10,582,713 B2
(45) Date of Patent: Mar. 10, 2020

(54) METHOD TO RAPIDLY DETECT INSECTS IN GRANULAR MATERIALS

(71) Applicant: UNIVERSITY OF MANITOBA, Winnipeg (CA)

(72) Inventors: Fuji Jian, Winnipeg (CA); Digvir Jayas, Winnipeg (CA); Paul Fields, Winnipeg (CA)

( * ) Notice: Subject to any disclaimer, the term of this patent is extended or adjusted under 35 U.S.C. 154(b) by 423 days.

(21) Appl. No.: 15/514,702

(22) PCT Filed: Sep. 25, 2015

(86) PCT No.: PCT/CA2015/050960
§ 371 (c)(1),
(2) Date: Mar. 27, 2017

(87) PCT Pub. No.: WO2016/044948
PCT Pub. Date: Mar. 31, 2016

(65) Prior Publication Data
US 2017/0231240 A1    Aug. 17, 2017

Related U.S. Application Data

(60) Provisional application No. 62/055,752, filed on Sep. 26, 2014.

(51) Int. Cl.
| | | |
|---|---|---|
| G01N 25/00 | (2006.01) |
| A23B 9/04 | (2006.01) |
| A01M 1/22 | (2006.01) |
| G01N 1/44 | (2006.01) |
| A01M 1/02 | (2006.01) |
| G01N 25/72 | (2006.01) |
| G01N 33/02 | (2006.01) |
| G01N 33/24 | (2006.01) |

(52) U.S. Cl.
CPC ............... *A23B 9/04* (2013.01); *A01M 1/026* (2013.01); *A01M 1/226* (2013.01); *G01N 1/44* (2013.01); *G01N 25/72* (2013.01); *G01N 33/02* (2013.01); *G01N 33/24* (2013.01)

(58) Field of Classification Search
USPC .................................................. 374/45, 100
See application file for complete search history.

(56) References Cited

U.S. PATENT DOCUMENTS

| | | | |
|---|---|---|---|
| 3,611,582 A | 10/1971 | Hamid et al. | |
| 6,073,365 A | 6/2000 | Halverson et al. | |
| 6,346,693 B1 * | 2/2002 | Kasevich | F26B 3/343 219/681 |
| 2004/0236267 A1 * | 11/2004 | Pierce | A23L 3/0055 604/20 |
| 2015/0236267 A1 * | 8/2015 | Hiroaki | H01L 51/0061 257/40 |

FOREIGN PATENT DOCUMENTS

CN    201094249    6/2008

* cited by examiner

*Primary Examiner* — Mirellys Jagan
(74) *Attorney, Agent, or Firm* — Michael R. Williams; Ryan W. Dupuis; Ade & Company Inc.

(57) ABSTRACT

A rapid method to detect and/or remove mobile insects inside granular material is presented. The core of this method is to heat grain samples to the desired temperatures (about 55 C) using microwave or radio frequency energy to force insects to move out of the granular material.

26 Claims, 4 Drawing Sheets

METHOD TO RAPIDLY DETECT INSECTS IN GRANULAR MATERIALS

PRIOR APPLICATION INFORMATION

The instant application is a 371 of PCT CA2015/050960, filed Sep. 25, 2015, which claimed the benefit of U.S. Provisional Patent Application Ser. No. 62/055,752, filed Sep. 26, 2014, entitled 'Method to Rapidly Detect Insects in Granular Materials", the contents of which are incorporated herein by reference.

BACKGROUND OF THE INVENTION

Microwave drying and heating of food, wood, ceramics, textile and pharmaceutical products is a common industrial practice. The microwave energy directly interacts with the processed materials to raise the interior temperature and significantly reduces treatment times as compared to conventional hot-water immersion or heated air methods.

Dielectric heating, which includes both radio frequency and microwave heating, has been investigated for insect disinfestation in stored grains and their derived products (Webber, Wangner, Pearson, 1946; Halverson, Burkholder, Bigelow, Norsheim, Misenheimer, 1996; Shayesteh & Barthakur, 1996; Nelson, 2001). Microwave treatment kills insects inside and outside grain kernels and also affects reproduction of survivors (Hamid, Kashyap, Cauwenberghe, 1968; Vadivambal, Jayas, White, 2007). However, the non-uniform temperature distribution of the processed materials limits its application on an industrial scale (Vadivambal & Jayas, 2007).

Researchers have investigated temperature distribution of food materials heated by microwaves (Sakai, Wang, Toba, Watanabe, 2004; Manickavasagan, Jayas, White, 2006; Gunasekaran & Yang, 2007; Nelson & Trabelsi, 2012). The uneven temperature distribution depends on many factors such as shape, volume, mass, chemical composition and moisture content of the processed food materials (Kelen, Ress, Nagy, Pallai, Pintye-Hodi, 2006). Dielectric properties of biological materials also depend on microwave frequency and composition, moisture content and temperature of the treated materials. The density of the processed material also affects its dielectric properties because different amounts of mass have different interactions with the electromagnetic fields. This is especially notable with particulate dielectric materials such as cereal grains, oilseeds, pulses (collectively referred to as grains) and soils. Consequently, temperature distribution is different from product to product, from equipment to equipment (Kelen et al., 2006) and from treatment to treatment.

The non-uniformity of microwave heating results in some hot spots with considerably higher temperature than average temperature. Manickavasagan et al. (2006) found that the temperature on the surface of treated wheat bulk was non-uniform. Furthermore, the maximum and minimum temperature and moisture distribution inside the treated wheat of different moisture contents by microwaves has not been reported.

There are several possible solutions to avoid the undesired non-uniformity of temperature and moisture content (Kelen et al., 2006), for example, intensification of the mixer motion and reduction of the microwave power. An increase in mixer motion can only decrease the non-uniformity to a certain degree, and domestic microwave ovens are usually equipped with a rotating plate. The use of microwaves for disinfestation of insect pests is based on the dielectric heating effect produced in grain and insect bodies. Insect bodies have higher moisture contents than stored grains and products derived from grains. The higher the water content, the higher the values of dielectric properties of a material. The dielectric loss factor of the insects was found to be much higher than that of stored grain and products (Nelson, 1991; Nelson & Whitney, 1960; Nelson, Stetson, Rhine, 1966; Ikediala, Tang, Wig, 2000; Rashkovan et al., 2003; Alfaifi, Tang, Rasco, Sablani, Jiao, 2013). The higher values of dielectric properties might result in higher temperatures inside insect bodies. The temperature difference between no-moveable model insect and walnut was about 4.6 to 6° C. (Wang, Tang, Johnson, Cavalieri, 2013). However, an insect body is smaller than treated grain kernels and heat inside an insect body might be transferred quickly to grain kernels during microwave treatment (Wang et al., 2013). Mobile insects such as adult rusty grain beetles, *Cryptolestes ferrugineus* (Stephens) (Coleoptera: Laemophloeidae), a common insect pest of moist stored grain throughout the world, are very sensitive to temperature and will escape when temperatures are high (Jian, Jayas, White, 2002).

During microwave treatment, insects move towards the surface from inside the treated wheat (Shayesteh & Barthakur, 1996). Insects were more active within a microwave field (Shayesteh & Barthakur, 1996). Heat plus light are used in Berlese funnel extraction of insects from stored grain (Berlese 1905). Therefore, microwave treatment might be used to force insects out without killing them. There is no study using microwave to expel insects.

Annually, over 2.6 billion tonnes of grains, including cereals, oilseeds and pulses, are grown. These products are then stored until they can be used by consumers. Most countries do not report how much grain is lost annually in storage and is not used for human consumption, but based on observations, these numbers are likely to be high (Jayas 2013). Losses occur when grain decays or is infested by pests, fungi or microbes, and physical losses are only part of the equation. Losses can also be economic, resulting from low prices and lack of access to markets for poor quality grain, or malnutrition and death of human being and animals, arising from poor quality or contaminated food. In some countries, grain cannot be sold if it is infested with insects (Canada, Australia) or grain is downgraded (USA)

Information on insect infestation inside stored grain is required for safe grain storage, before and after insect control, before grain loading and unloading, and during domestic and international sales and transportation. Detecting insect infestation is difficult under most grain storage conditions.

Storage management greatly influences pest development and control within grain. It encompasses decisions upon the location of stores, storage periods and the quality control objectives for stored commodities. All of these have substantial implications for pest management and are components of the complex interactive network of factors affecting loss reductions in grain storage.

Grain monitoring plays an imperative role in the development of pests in grain. For example, if we can monitor grain effectively, we can develop a sound integrated pest management (IPM) program and better solutions to grain storage problems. Therefore, information on insect infestation inside grain is required for safe grain storage, before and after chemical and physical insect control, before grain loading and unloading, and during domestic and international trading negotiation and transportation. To detect insect infestation inside grain held in grain storage structures such as bins (silos), trucks, railcars, ships, vessels, containers, and bags, grains are usually sampled using mechanical and manual devices. The sampled grain is further investigated inside the laboratory using the naked eye and/or equipment. However, the shaking and naked eye method cannot detect hidden insects. To detect both hidden and external insects, the following methods are suggested: flotation and cracking (Brader et al., 2002), acoustic sensor (Gutierez et al., 2010), immunoassay (Krizkova-Kudlikova and Hubert, 2008; Atui et al., 2007), single kernel characterization (SKCS) (Pearson et al., 2003), electrical conductance (Brabec et al., 2010; Pearson and Brabec, 2007), near-infrared hyperspectral imaging (Singh et al., 2009), and soft –X ray roentgenography (Karunakaran, et al. 2004, Nawrocka et al., 2012). None of these recommended methods is commercialized or used by grain industry due to some of the following disadvantages: high cost, limited capacity, intensive labor, time consuming, and low accuracy.

The most used and commercialized process is the Berlese funnel method and this method is also widely used in separation of insects from soil and other biomass materials. The Berlese funnel method uses an incandescent light bulb to provide heat that forces insects to exit grain kernels (Berlese, 1905). Problems with this method include that it takes at least 6 hours; collects only 30-70% of insects in the grain samples (Minkevich et al., 2002); incandescent light bulbs are being phased-out; and it requires extensive space for running multiple samples. Thin or multi layers soil, grains, processed granular foods, and breakfast cereals were suggested to increase the accuracy and efficiency of the Berlese funnel method. However, these modified methods did not increase its detection accuracy (Minkevich et al., 2002). The modified methods also require at least 1 h. Therefore, the Berlese funnel method cannot be used when immediately (e.g. in less than half hour) evaluation of grain infestation is required. Before grain loading and unloading at farms, elevators, and terminals, further actions will depend on whether there are insects inside the grain samples. In Canada, the Beriese funnel method is used for detection of infestation and infested grain must be treated (Canada Grain Act, 1994). Waiting for the determination of insect infestation increases handling and transportation cost. Therefore, a rapid method to detect insects inside sampled grain with larger capacity and higher accuracy is required.

SUMMARY OF THE INVENTION

According to an aspect of the invention, there is provided a method of testing a quantity of a granular material for insect infestation comprising:

subjecting a quantity of granular material to sufficient microwave or radio frequency energy to heat the entire quantity of granular material to an average temperature of between 45-65° C.;

maintaining the quantity of grain at said temperature for a period of time; and detecting any insects exiting the granular material.

According to a further aspect of the invention, there is provided a method of treating a quantity of a granular material for insect infestation comprising:

subjecting a quantity of granular material to sufficient microwave or radio frequency energy to heat the entire quantity of granular material to an average temperature of between 45-65° C.;

maintaining the quantity of granular material at said temperature for a period of time; and separating any insects exiting the granular material from the granular material.

In some embodiments, the granular material is selected from the group consisting of grains and soil. The grains may be for example but by no means limited to cereal grains, oilseeds and pulses.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

A rapid method to detect and/or remove mobile insects inside granular material is presented. The core of this method is to heat grainular material (in some embodiments, samples of about 1 kg, although any suitable size sample may be used) to the desired temperatures (a temperature that is sufficient to force the insects to exit the granular material but not sufficient to damage the grain, for example, about 45-65° C. or 50-60° C. or about 55° C.). This may be done inside a microwave oven although any suitable source of microwave or radio frequency energy may be used. As discussed herein, this forces insects to move out of the granular material, for example, soil or grains such as cereal grains, oilseeds, pulses or the like. In some embodiments, there is provided means to separate the expelled insects from the granular material, for example, a collection pan or collector connected to the bottom of a substantially air-tight container. As discussed herein, the granular material is kept at the desired temperature for at least 15 min.

Thus, described herein is a method by which a sample of a quantity of granular material, for example, processed granular foods, breakfast cereals, food grains, oilseeds, soil, feed grains and/or leguminous seeds, can be tested for insect infestation. For example, a sample of the granular material can be tested during storage, prior to transport, prior to sale or purchase and/or prior to combination with other granular material.

Figure 4:
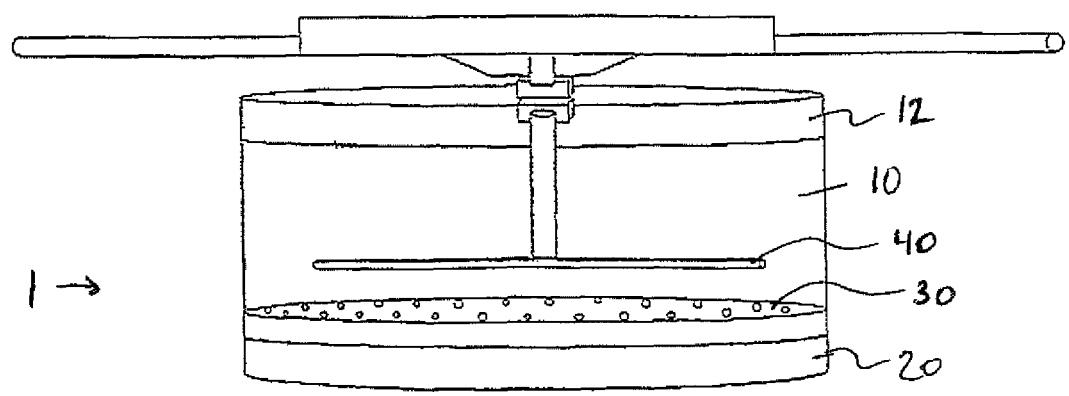
FIG. 4. Schematic drawing showing one embodiment of a device for carrying out the method of the invention.

One exemplary embodiment of the container 1 is shown in FIG. 4. As shown therein, container 1 comprises an upper chamber 10 for holding a quantity of a granular material therein and a lower chamber 20 for collecting insects. The upper chamber 10 and the lower chamber 20 are separated by a perforated floor 30. The upper chamber 10 further comprises a mixing rod 40 for stirring the granular material during the method as discussed herein.

For use, the upper chamber 10 and the lower chamber 20 are fitted together such that the container 1 is substantially air-tight. The upper chamber 10 also has a lid 12 which is removed when the sample is placed in the upper chamber 10.

Prior to use, the sample of the granular material is placed in the upper chamber 10 with the mixing rod inserted therein. As discussed above, the upper chamber 10 and the lower chamber 20 are fitted together such that the container 1 is substantially air-tight.

The container 1 is then heated, for example, in a conventional microwave, for a a period of time. Specifically, the sample in the container 1 is heated for a period of time that is sufficient to heat the granular material to a temperature of approximately 40-65° C., as discussed herein. For example, the container 1 may be heated for approximately 30-120 seconds.

Once heated, the container is then left to stand for an additional period of time, for example, 15 minutes, during which time the temperature within the container is maintained at a temperature between 40-65° C. as a result of heated vapor generated during the heating phase being retained in the substantially air-tight container 1.

As discussed above, the mixing rod 40 stirs the sample of the granular material during the heating process and the subsequent incubation period. As discussed herein, this mixing promotes more even temperature distribution throughout the container.

As discussed herein, exposure of the sample of the granular material to this temperature is sufficient to drive insects infesting the granular material out of the granular material.

As discussed above, the upper chamber 10 and the lower chamber 20 are separated by a perforated floor 30. As discussed herein, the exact size and distribution of the perforations can be varied provided that the perforations are smaller in diameter than the average diameter of an individual granule of the granular material being analyzed so that the passage of granular material from the upper chamber 10 to the lower chamber 20 is minimized. Furthermore, the perforations must be of a size and/or shape such that an infesting insect can pass therethrough and into the lower chamber 20.

Thus, as the sample of the granular material in the container 1 is heated, any infesting insects will exit the granular material. As these insects encounter the perforated floor 30, they are able to pass through a perforation in the floor, thereby leaving the upper chamber 10 for the lower chamber 20.

As will be apparent to one of skill in the art, the container is substantially air-tight in that it retains steam or heated air generated within the container 1 during the heating process. Loss of some heated air is acceptable provided that the temperature of the granular material is maintained at the desired temperature for a sufficient period of time such that at least some infesting insects are driven out of the granular material and into the lower chamber 20.

As will be apparent to one of skill in the art, the container 1 is preferably made of a microwaveable material, that is, a material that is not significantly altered by exposure to microwave energy.

As will be apparent to one of skill in the art, the shape and/or dimensions of the container 1 are relatively unimportant provided that the container will fit in most conventional microwave ovens and can hold a sufficient quantity of granular material for testing. As will be appreciated by one of skill in the art, larger samples are more preferred.

As will be appreciated by one of skill in the art, this provides information on infestation much more quickly that for example the Burlese funnel method. Furthermore, aside from the container, no specialized equipment is necessary. Consequently, a sample from a quantity of granular material can be checked for infestation prior to transport or combining with other granular material, thereby preventing the spread of infestation.

As discussed herein, the sample is subjected to a temperature that will not impair subsequent germination of any seeds, meaning that the sample can be returned to the granular material following testing. Furthermore, as discussed herein, the container 1 can be used in a conventional microwave oven, meaning that testing can be carried out quickly and easily virtually anywhere there is access to a microwave oven. This means that more frequent testing can be carried out if desired and the quicker processing time means reduced handling and quicker shipping.

According to an aspect of the invention, there is provided a method of testing a quantity of granular material for insect infestation comprising:

subjecting a quantity of granular material to sufficient microwave or radio frequency energy to heat the entire quantity of granular material to an average temperature of between 45-65° C.;

maintaining the quantity of granular material at said temperature for a period of time; and detecting any insects exiting the granular material.

In some embodiments, the period of time is at least 15 minutes.

In some embodiments, the quantity of granular material is heated in a sealed container which retains vapor released from the granular material during heating. This in turn promotes a more even temperature range within the container and facilitates maintaining the granular material at the desired temperature, as discussed herein.

In some embodiments, there is provided a collector beneath the perforated floor for retaining the insects.

In some embodiments, the quantity of granular material is mixed during heating.

In some embodiments, the quantity of granular material is mixed by stirring.

In some embodiments, the stirrer may be arranged to stir the granular material during the initial heating phase (wherein the microwave and/or radio frequency energy is applied to the granular material) as well as during the maintenance phase (wherein the granular material is kept at the desired temperature) to ensure that an approximately even temperature distribution is attained.

According to a further aspect of the invention, there is provided a method of treating a quantity of a granular material for insect infestation comprising:

subjecting a quantity of granular material to sufficient microwave or radio frequency energy to heat the entire quantity of granular material to an average temperature of between 45-65° C.;

maintaining the quantity of granular material at said temperature for a period of time; and separating any insects exiting the granular material from the granular material.

In some embodiments, the granular material is selected from the group consisting of grains and soil. The grains may be for example but by no means limited to cereal grains, oilseeds and pulses. In some embodiments, the grains are wheat and barley.

As will be apparent to one of skill in the art, temperatures below 45° C. are insufficient to drive insects from the granular material, for example, grains. Furthermore, exposure to temperatures above 65° C. may reduce the quality of certain grains. Consequently, in some embodiments, a temperature between 50-60° C. is used or a temperature of approximately 55° C. is used.

It is of note that one of skill in the art can determine the amount of energy of microwave and/or radio frequency energy necessary to heat a desired quantity of granular material to the desired temperature through routine experimentation and/or calculation, as discussed herein.

As will be appreciated by one of skill in the art, the specific moisture content of the granular material used in the invention does not matter. This is because granular material that has for example less than 9% moisture content will likely also be too dry for insect infestation. However, in some embodiments, water may be added to the sample prior to testing.

Furthermore, the insect to be detected and/or removed using the method of the invention may be any insect that infects or infests granular material including stored-product insects As discussed above, the perforations on the floor of the sealed container are of a sufficient size such that the exiting insects pass through while the granulated material, for example, the grains, cannot pass through and are retained within the sealed container.

For example, the perforations may be approximately 1-3 mm in diameter or 2-3 mm in diameter or may be approximately 2.7 mm in diameter. As will be apparent to one of skill in the art, the perforations do not necessarily need to be circular or any other regular shape provided that the perforations allow the passage of the insects from the upper chamber to the lower chamber attached thereto.

To easily identify the collected insects, a small amount (about 50 ml) of water can be added to the collection pan after the microwave treatment. The collection pan can be investigated under a microscope or by using the naked eye.

Irrespective of the method of grain sample collection, this process can be used. The entire process requires less than 30 minutes and can collect more than 99% of mobile adults and 80% mobile larvae. Consequently, this invention could be used at the farms, elevators, and terminals (grain handling facilities) to test incoming or stored grain, thereby reducing losses due to insect infestation and increasing shipping efficiencies by reducing the time spent waiting for samples to be tested.

Also described herein is the 3-D distribution of macroscopic temperature and moisture content of wheat with different moisture content which was treated by using different microwave treatment times and methods (continuous or intermittent treatment). The percentage of insects expelled and sieved out of the treated wheat was measured and the treatment effect was determined after a two month incubation of the treated wheat, as discussed below.

The invention will now be further described by way of examples; however, the invention is not necessarily limited to the examples.

EXAMPLES

Preliminary Study

Wheat with 14, 16 and 18% moisture content was continuously or intermittently treated inside a microwave oven at 1.1 kW and 2.45 GHz with 30, 60 and 90 s treatment times. Three dimensional distributions were determined by measuring temperatures and moisture contents at 27 locations inside a 10×9×9 cm$^3$ plastic container without covering. Twelve and 25 d after the introduction of adults of *Cryptolestes ferrugineus*, the infested wheat was heated inside the microwave oven, and the escaped adults and larvae were counted and the treated wheat was shaken to sieve out the adults and larvae which did not escape from the wheat. After this separation, the wheat was incubated at 30±1° C. and 75±5% RH for 2 months. Insects inside the incubated wheat were counted.

The measured temperatures of the treated wheat had no significant differences among replicates when the wheat with different moisture contents was continuously or intermittently treated except for the 30 s continuous treatment (Table 1). The measured moisture content of treated wheat had significant differences between replicates, except for the wheat which was intermittently treated, and 14% and 16% MC wheat which was continuously treated for 90 s (Table 1). There was significant difference in both temperature and moisture content between intermittent and continuous treatment methods (Table 2). These results indicated that continuous treatment with a short treatment time generated a different distribution of temperatures and moisture content from treatment to treatment. When treatment time was long, temperature and moisture content had similar mean, maximum and minimum values in different replicates. This was one of the reasons the insects were continuously and intermittently treated for 90 s in this preliminary study.

The difference between maximum and minimum temperatures and moisture content of continuously treated wheat increased with increasing treatment time (Table 3) as reported elsewhere (Gunasekaran & Yang, 2007; Kelen et al., 2006; Sakai et al., 2004). This difference was not reduced when the wheat was intermittently treated (Table 3). The intermittently treated wheat had a higher temperature and a lower moisture content than the continuously treated wheat. These results indicated that the wheat lost more water after intermittent treatment (Table 3). Thus, intermittent treatment did not generate more even distribution of temperatures and moisture content. This conclusion was contradictory to the report by Shayesteh and Barthakur (1996). With the same treatment time, higher moisture contents would reduce this difference. This means that wet grain could produce a more even distribution of temperature and moisture content. These results were consistent with the theory of dielectric heating. Wheat inside the container was mixed before the treatment, so the non-uniform distribution of temperature and moisture content was mostly caused by the non-uniformity of the generated microwave energy.

Figure 2:
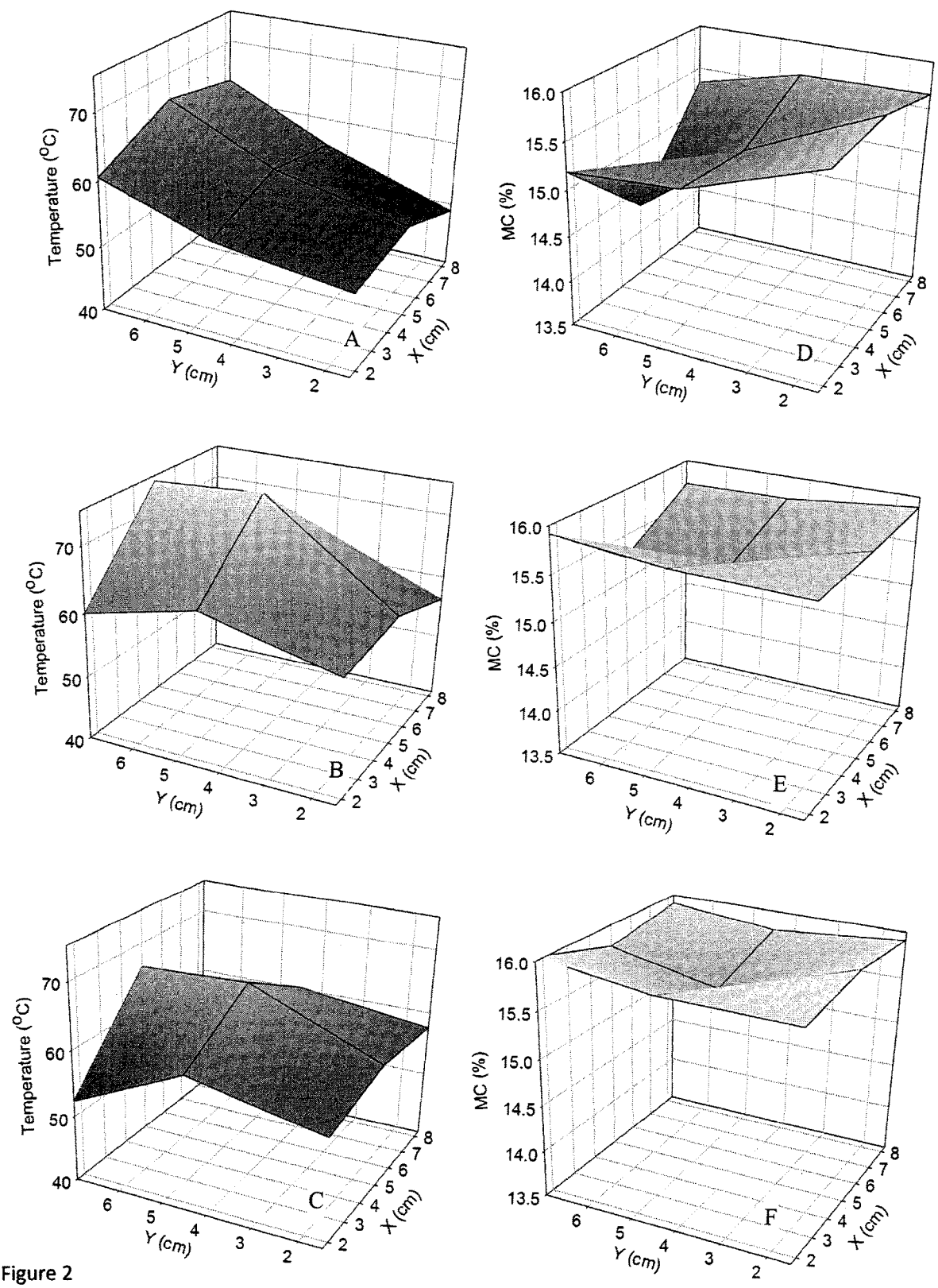
FIG. 2. Temperatures (A, B and C) and moisture contents (D, E and F) at the top (A and D), middle (B and E) and bottom (C and F) layers of the 16% MC wheat microwave-treated continuously for 90 s inside the container. Data show one replicate which had the smallest minimum moisture contents.
Figure 3:
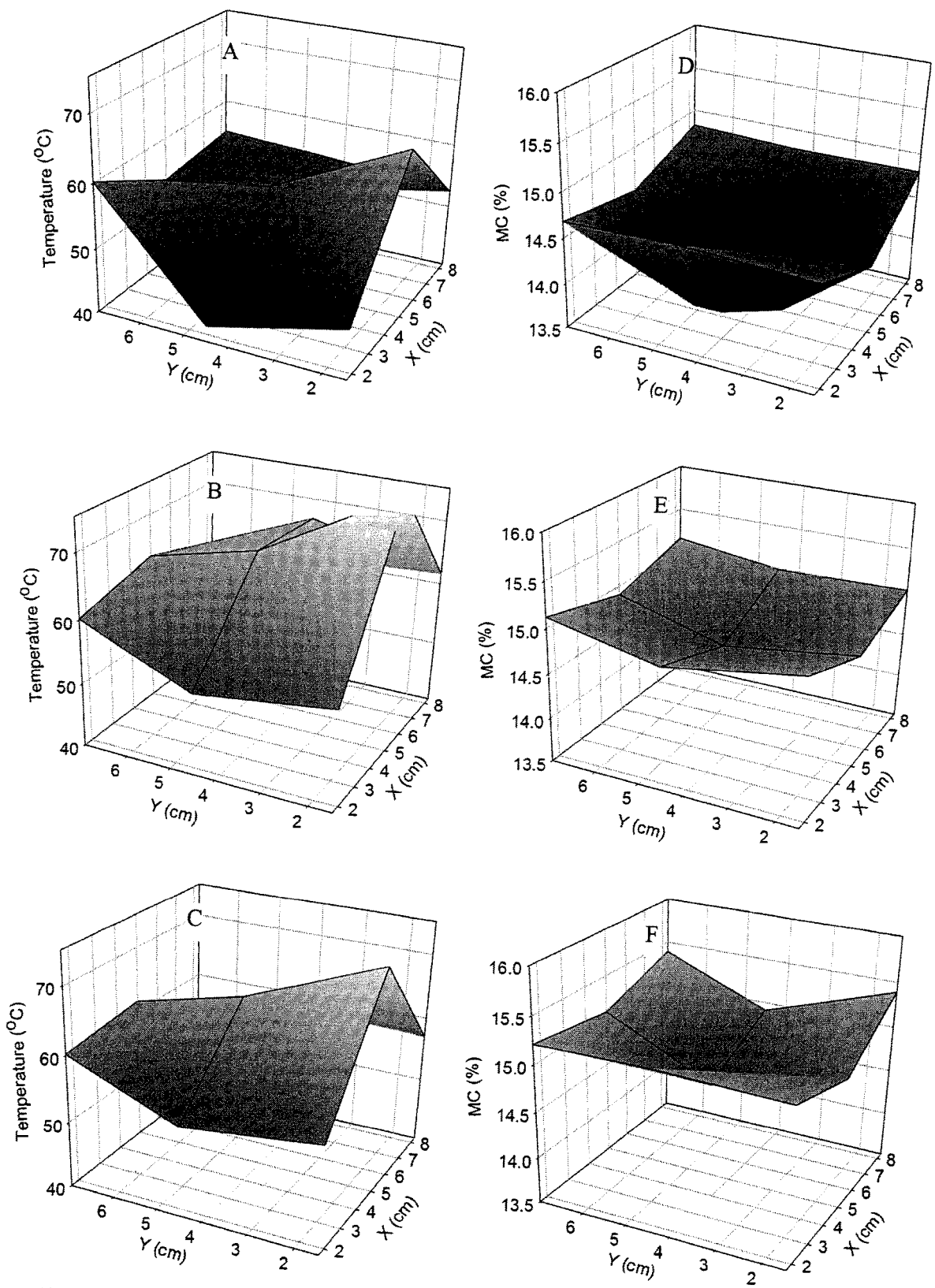
FIG. 3. Temperatures (A, B and C) and moisture contents (D, E and F) at the top (A and D), middle (B and E) and bottom (C and F) layers of the 16% MC wheat microwave-treated intermittently for 90 s inside the container (60 s treatment, 5 min no treatment followed by 30 s treatment). Data show one replicate which had the smallest minimum moisture contents.

In all of the 36 replicates, the maximum temperature was located at the middle layer with one exception, while the minimum temperature was located at the top layer, with five exceptions (Table 3). Manickavasagan et al. (2013) also found the internal temperature of the dates was higher than the surface temperature. The minimum moisture content was located at the top layer with five exceptions. This might be explained by a grain drying effect from the microwave energy. During the beginning of heating, all of the microwave energy supplied to the wheat might be used to increase the grain temperature. The drying process only took place once the temperature was high enough for moisture evaporation to take place. This result was supported by the negative correlation between temperature and moisture content at each location of the treatment (Table 4). This negative correlation increased with the increase of treatment time (Table 4). Thus, longer treatment time generated dry and hot spots at the same position (FIG. 2), even though the hot and dry spots were not always at the same position in different replicates. Grain quality might decrease inside the hot and dry spots (Vadivambal & Jayas, 2007). The minimum temperature after 90 s treatment was only about 45 to 47° C. Insects might survive inside the cold and wet spots because 18 h is required to kill all of the adults at 47° C. (Jian et al., 2002). However, adults would migrate to the cooler and damper spots (Jian et al., 2002).

Insect Extraction or Expelling Effect

More than 20% of adults and larvae were expelled by 60 s microwave-treatment (Tables 5 and 6). During microwave heating, most of the expelled adults and larvae escaped from the bottom and the top of the wheat bulk. This result could be explained by the elevated temperatures after microwave treatment. Some of the expelled adults were also killed by the subsequent microwave-treatment (Table 5). After 60 s microwave-treating and sieving, 100% adults and ≥99% larvae were separated from the wheat (Tables 5 and 6). These results indicated that adults or larvae could be expelled or separated out after microwave-treating and sieving.

When the number of insects expelled and captured by sieving were compared, there was no significant difference between intermittent or continuous treatment methods at any moisture content of wheat (Table 7), or among any microwave-treatment times (Table 8). Therefore, microwave heating could expel insects if grain is warmed.

When microwave treatment times were ≥60 s, only a few larvae were extracted by the Berlese funnel method (Table 6). There were significant differences in the number of insects extracted by the Berlese funnel method between 30 s with 60 s or 90 s of microwave treatment times, while there were no significant differences between 60 s and 90 s. These results indicated that 30 s treatment was not enough to expel insects. Jian et al. (2002) found adults of C. ferrugineus moved away from warmer (>37.5° C.) grain. After microwave heating, the temperature at more than 90% of the grain sample was higher than 37.5° C. if treatment time was ≥60 s (Table 3). These results explained the expelling effect of the microwave treatment.

Disinfestation Effect

If the insects survived the microwave-treatment, they could multiply during the two month incubation. Only a few adults and larvae were separated from the microwave-treated wheat after the incubation period, while more than 600 insects (adults and larvae) were isolated from the wheat which was not microwave-treated (Table 5). Compared with the control, less than 24% of insects multiplied inside the microwave-treated wheat during the two month incubation. If the wheat was continuously treated for 90 s, less than 7.2% insects multiplied inside the microwave-treated wheat. This reduced multiplication was caused by the disinfestation effect of microwave treatment on the larvae and eggs because all of the adults were separated.

Microwave treatment was not able to kill 100% of the insects (includes adults, larvae and eggs); however, the number of their offspring was significantly decreased after insects were expelled and separated out of the microwave-treated wheat (Table 5).

Shayesteh and Barthakur (1996) observed significant differences (with some exceptions) between mortalities of *Tribolium confusum* and *Plodia interpunctella* treated continuously and intermittently. Our study showed that there was no difference in the 3-D distribution of temperature and moisture content or in the mortality of insects between intermittent and continuous treatments. This difference might be caused by the different treatment times, power levels and amount of grain used. The temperature reported by Shayesteh and Barthakur (1996) was 39 to 94° C. and they did not observe any hot spot in more than 100 h of temperature recording. They used 50 g of wheat and measured temperature at only one location. About 830 g wheat was used in our study. To disinfest grain, therefore, larger amounts of grain could be microwave-treated to expel and sieve out infested insects. Compared with larger insects, the mortality of *C. ferrugineus* was low due either to a low probability of direct microwave absorption or hiding of the insects in cooler spots (Shayesteh & Barthakur, 1996; Vadivambal et al., 2007). When 100% mortality inside 50 g wheat is reached, the maximum temperature is about 107 to 114° C. and the average temperature is about 80 to 86° C. (Vadivambal et al., 2007). Other researchers also reported similar temperatures when grain is treated under susceptible power levels and exposure times (Hamid & Boulanger, 1969; Locatelli & Traversa, 1989). However, these temperatures reduce the germination of wheat to less than 11% (Vadivambal et al., 2007). Therefore, it might be a challenge to disinfest insects with 100% mortality without influencing grain germination and quality.

The main reason for killing of insects by microwave energy may be the high temperatures of the treated materials and insect bodies (Locatelli & Traversa, 1989; Shayesteh & Barthakur, 1996). This is supported by the fact that power levels and exposure times have been identified as two important parameters to control insects with 100% mortality (Bedi & Singh, 1992). Our study showed less than 100% mortality of larvae inside the wheat with 90 s treatment time and the maximum temperature was 88° C. The maximum temperature is higher than the insect's lethal temperature, but the minimum temperature is not (Fields, 1992). Grain germination and quality will be influenced under this maximum temperature (Vadivambal et al., 2007; Vadivambal & Jayas, 2007). Consequently, to maintain grain quality, microwave treatment with lower than the susceptible power level and exposure time should be used to expel and sieve insects out of the treated materials. This, the insects are expelled from the grain without killing the insects and more importantly without negatively influencing grain quality. From the point of view of insect disinfestation, driving the insects out of the treated materials has the same effect as killing insects.

Furthermore, forcing an insect out of the treated materials will use less power and exposure time which in turn means that the treatment will not influence grain quality. Insects are unlikely to develop resistance to lower than the susceptible power level and exposure time (Watters, 1976). Therefore, driving insects out of stored products could be an alternative method for insect disinfestation.

Conclusions of the Study

Temperature and moisture content had similar mean, maximum and minimum values in different replicates when microwave-treatment time was long (90 s).

Intermittent treatment did not generate a more even distribution of temperature and moisture content, while wet grain (>16% MC) treated in a microwave oven did generate a more even distribution.

A longer treatment time (90 s) generated dry and hot spots at the same position but the hot or dry spots were not always at the same position in different replicates.

All of the introduced adults were expelled and separated out after microwave treatment and there was no significant difference between intermittent or continuous treatment methods.

Microwave treatment was not able to kill all insects; however, the number of offspring was decreased by >75%.

Materials and Methods of the Preliminary Study

Adults of *C. ferrugineus*, obtained from the Cereal Research Center, Agriculture and Agri-Food Canada, Winnipeg, were used in the experiments. Insects were reared inside a bulk of 3 kg whole wheat (the same wheat as used in the tests) at room temperature and 70±5% RH for two to three months. One hundred adults (mixed ages and sexes) were selected using a gentle vacuum at room temperature. The selected adults were directly introduced into the tempered wheat held in 4-L bottles.

Microwave Treatment, Moisture Content and Temperature Measurement

Figure 1:
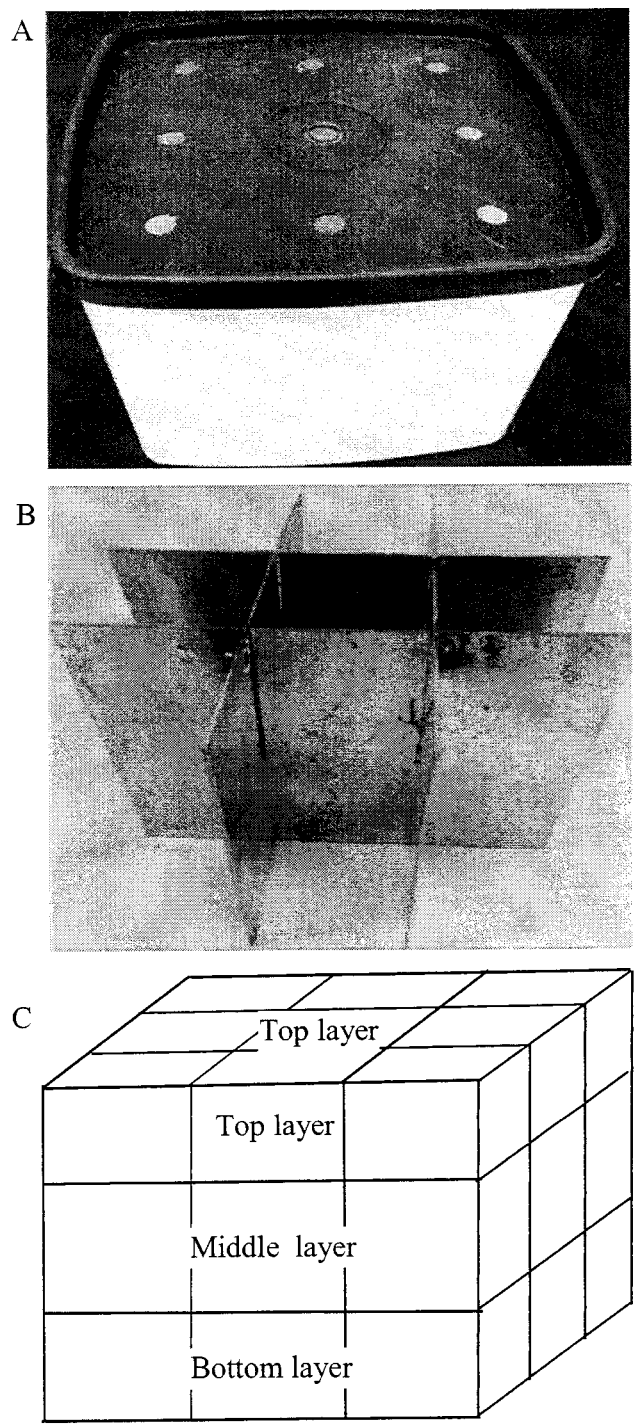
FIG. 1. The plastic container (A) was separated into nine sections after a metal grid (B) was inserted into the container. Each section was further separated into top, middle and bottom layers (C). The holes in the lid of the container were used to insert the thermocouples.

Wheat (about 830 g) with or without insects was treated inside plastic containers (FIG. 1). These plastic containers were purchased from a local grocery store. The total volume of the container was 810 cm$^3$ with inner dimension of 10 cm length, 9 cm width and 9 cm depth. The lid of the container was perforated with nine holes (3.7 mm diameter). The holes were evenly distributed in the lid and used to insert thermocouples after microwave treatment (FIG. 1). During microwave treatment, the lid was not on the container. The bottom of the container was also perforated with 90 holes (2.7 mm diameter). These holes were evenly distributed on the bottom of the container and allowed insects to exit. During microwave treatment, the plastic container was placed inside another plastic container which had no holes on its bottom. There was a 0.2 cm gap at the bottom of these two containers. The outside container was used to collect the expelled insects.

A GE domestic microwave oven (JES1145WTCT, Thomson, Inc. Marietta, Ga., USA) with 2.45 GHz and operated at 1.1 kW output power was used for all experiments. The oven was equipped with a rotating plate and the plastic container was centered on the rotating plate. To evaluate the power output of the microwave oven, a glass container with 500 mL water was heated by the microwave for 30, 60 or 90 s continuously. The temperatures of the water at the beginning and the end of the microwave treatment were measured and power output of the microwave was calculated using a standard (British Standards Institution, 2012) for all three heating times and mean values were reported:

$$p = \frac{4.187 m_w (T - T_0) + 0.55 m_c (T - T_0)}{t}$$

Where;
P=power output of the microwave (W);
$m_w$=mass of the water (g);
$m_c$=mass of the glass container (g);
$T_0$=the temperature before microwave treatment (° C.);
T=temperature after microwave treatment (° C.);
t=treatment time (s).

Thermocouples (T type, Thermo Electric Canada, LTD, Ontario, Canada, accuracy ±0.5° C.) were used to measure the wheat and water temperature. Three thermocouples were fixed on a 0.1 cm diameter steel rod and the thermocouples were located at 2, 5, and 8 cm from the bottom of the rod.

Twenty eight thermocouples were connected to a data acquisition system (34970A Data Acquisition system, Agilent Technologies, Inc., Santa Clara, Calif., USA) and temperatures were recorded at 20 s intervals. Twenty seven thermocouples were used to measure the wheat temperatures inside the container and one thermocouple was used to measure room temperature.

Thermocouples were calibrated by using an ice-water mixture and boiling water. When the nine metal rods were inserted into the plastic container through the nine holes in the lid, the temperatures inside the container at 27 locations were measured (FIG. 1). These measured temperatures represented the 3-D temperature distribution of the treated wheat at the end of the treatment inside the plastic container.

Wheat moisture contents at the 27 locations were measured after the temperature measurement.

To sample the wheat at the 27 locations, a metal grid which separated the container into 9 equal sections was inserted into the plastic container. Top, middle and bottom wheat from each section was removed using a spoon, and moisture content of the sampled wheat was determined (ASABE, 2009).

While the preferred embodiments of the invention have been described above, it will be recognized and understood that various modifications may be made therein, and the appended claims are intended to cover all such modifications which may fall within the spirit and scope of the invention.

REFERENCES

Alfaifi, B., Tang, J., Rasco, B., Sablani, S., & Jiao, Y. (2013). Radio frequency disinfestation treatments for dried fruit: dielectric properties. Food Science and Technology, 50, 746-754.

ASABE. (2009). Standard S352.2: Moisture measurement—Unground grain and seeds. St. Joseph, Mich.: ASABE.

Atui, M. B., Flinn, P. W., Lazzari, S. M. N., Lazzari, F. A., 2007. Detection of Rhyzopertha dominica larvae in stored wheat using ELISA: the impact of myosin degradation following fumigation. Journal of Stored Products Research 43, 156-159

Bedi, S. S., & Singh, M. (1992). Microwaves for control of stored grain insects. National Academy of Science Letter, 15, 195-197.

Berlese, A. (1905). Apparecchio per raccogliere presto ed in gran numero piccoli Artropodi. Redia, 2, 85-90.

Brabec, D., Pearson, T., Flinn, P., Katzke, D., 2010. Detection of internal insects in using a conductive roller mill and estimation of insect fragments in the resulting flour. Journal of Stored Products Research 46, 180-185.

Brader, D., Lee, R. C., Plarre, R., Burkholder, W., Kitto, G. B., Kao, C., Polston, L., Dorneau, E., Szabo, I., Mead, B., Rouse, B., Sullins, D., Denning, R., 2002. A comparison of screening methods for insect contamination in wheat. Journal of Stored Products Research 38, 75-86.

British Standards Institution. (2012). BS EN 60705:2012: Household microwave ovens-methods for measuring performance. BSI Standards Limited, London, UK.

Fields, P. G. (1992). The control of stored-product insects and mites with extreme temperatures. Journal of Stored Products Research, 28, 89-118.

Gutierez, A., Ruiz, V., Molto, E., Tapia, G., der Mar Tellez, M., 2010. Development of a bioacoustic sensor for the early detection of red palm weevil (*Rynchophorus ferrugineus* Olivier). Crop Protection 29, 671-676.

Gunasekaran, S., & Yang, H. W. (2007). Effect of experimental parameters on temperature distribution during continuous and pulsed microwave heating. Journal of Food Engineering, 78, 1452-1456.

Halverson, S. L., Burkholder, W. E., Bigelow, T. S., Norsheim, E. V., & Misenheimer, M. E. (1996). High-power microwave radiation as an alternative insect control method for stored products. Journal of Economic Entomology, 89, 1638-1648.

Hamid M. A. K., & Boulanger, R. J. (1969). A new method for the control of moisture and insect infestations of grain by microwave power. Journal of Microwave Power, 4, 11-18.

Hamid, M. A. K., Kashyap, C. S., & Cauwenberghe, R. V. (1968). Control of grain insects by microwave power. Journal of Microwave Power, 3, 126-135.

Ikediala, J. N., Tang, J., & Wig, T. (2000) A heating block system for studying thermal death kinetics of insect pests. Transactions of the ASAE, 43, 351-358.

Jian, F., Jayas, D. S., & White, N. D. G. (2002). Temperature and geotaxis preference by *Cryptolestes ferrugineus* (Coleoptera: Laemophloeidae) adults in response to 5° C./m temperature gradients at optimum and hot temperatures in stored wheat and their mortality at high temperatures. Environmental Entomology, 31, 816-826.

Jian, F., Jayas, D. S., & White, N. D. G. (2013). Specific heat, thermal diffusivity, and bulk density of genetically modified canola with high oil content at different moisture contents, temperatures, and storage times. Transaction of the ASABE, 56, 1077-1083.

Karunakaran, C., Jayas, D. S., White, N. D. G., 2004. Identification of wheat kernels damaged by the red flour beetle using X-ray images. Biosystems Engineering 87, 1-8.

Kelen, A., Ress, S., Nagy, T., Pallai, E.,& Pintye-Hodi, K. (2006). Mapping of temperature distribution in pharmaceutical microwave vacuum drying. Powder Technology, 162, 133-137.

Krizkova-Kudlikova, I., Hubert, J., 2008. Development of polyclonal antibodies of the detection of *Tribolium castaneum* contamination in wheat grain. Journal of Agricultural and Food Chemistry 56, 8035-8040.

Locatelli, D. P., & Traversa, S. (1989). Microwaves in the control of rice infestants. Italian Journal of Food Science, 1, 62.

Manickavasagan, A., Jayas, D. S., & White, N. D. G. (2006). Non-uniformity of surface temperatures of grain after microwave treatment in an industrial microwave dryer. Drying Technology, 24, 1559-1567.

Manickavasagan, A., Alahakoon, P. M. K., Al-Busaidi, T. K., Al-Adawi, S., Al-Wahaibi, A. K., Al-Raeesi, A. A., Al-Yahyai, R. & Jayas, D. S. (2013). Disinfestation of stored dates using microwave energy. Journal of Stored Products Research, 55, 1-5.

Nawrocka A., E. Stepien, S. Grundas, and J. Nawrot, 2012. Mass loss determination of wheat kernel infested by granary weevil from X-ray images. Journal of Stored Products Research 48, 19-24.

Minkevich J. M., C. J. Demianyk, N. D. G. White, D. S. Jayas, B. Timlick. A rapid method to detect *Cryptolestes ferrugineus* (Coleoptera: Cucujidae) larvae in stored grain. Canadian Journal of Plant Science, 2002, 82(3): 591-597, 10.4141/P01-106.

Nelson, S. O. (1991). Dielectric properties of agricultural products: measurements and applications. IEEE Transactions on Electrical Insulation, 26, 845-869.

Nelson, S. O. (2001) Radio-frequency and microwave dielectric properties of insects. Journal of Microwave Power and Electromagnetic Energy, 36, 47-56.

Nelson, S. O., Stetson, L. E., & Rhine, J. J. (1966). Factors influencing effectiveness of radiofrequency electric fields for stored-grain insect control. Transactions of the ASAE, 9, 809-815.

Nelson, S. O., & Trabelsi, S. (2012). Factors influencing the dielectric properties of agricultural and food products. Journal of Microwave Power and Electromagnetic Energy, 46, 93-107.

Nelson S. O., & Whitney, W. K. (1960). Radiofrequency electric fields for stored grain insect control. Transactions of the ASAE, 3, 133-137.

Pearson, T. C., Brabec, D. L., Schwartz, C. R., 2003. Automated detection of internal insects infestations in whole wheat kernels using a Perten SKCS 4100. Applied Engineering in Agriculture 19, 727-733.

Pearson, T. C., Brabec, D. L., 2007. Detection of wheat kernels with hidden insect infestations with an electrically conductive roller mill. Applied Engineering in Agriculture 19, 727-733.

Rashkovan, V. M., Khizhnyak, N. A., Basteev, A. V., Bazyma, L. A., Niño de Rivera, L., & Ponomaryova, I. A. (2003). Interaction of electromagnetic waves with granular agricultural product and insects. Journal of Microwave Power and Electromagnetic Energy, 38, 1-12.

Sakai, N., Wang, C., Toba, S., & Watanabe, M. (2004). An analysis of temperature distributions in microwave heating of foods with non-uniform dielectric properties. Journal of Chemical Engineering of Japan, 37, 858-862.

SAS. (2010). SAS User Guide, release 9.22. Cary, N.C.: SAS Institute.

Shayesteh, N., & Barthakur, N. N. (1996). Mortality and behaviour of two stored-product insect species during microwave irradiation. Journal of Stored Products Research, 32, 239-246.

Singh, C. B., Jayas, D. S., Paliwal, J., White, N. D. G., 2009. Detection of insect-damaged wheat kernels using near-infrared hyperspectral imaging. Journal of Stored Products Research 45, 151-158.

Vadivambal, R., & Jayas, D. S. (2007). Changes on quality of microwave-treated agricultural products—a review. Biosystems Engineering, 98, 1-16.

Vadivambal, R., Jayas, D. S., & White, N. D. G. (2007). Wheat disinfestation using microwave energy. Journal of Stored Products Research, 43, 508-514.

Wang S., Tang, J., Johnson, J. A., & Cavalieri, R. P. (2013). Heating uniformity and differential heating of insects in almonds associated with radio frequency energy. Journal of Stored Products Research, 55, 15-20.

Watters, F. L. (1976). Microwave radiation for control of *Tribolium confusum* in wheat and flour. Journal of Stored Products Research, 12, 19-25.

Webber, H. H., Wangner, R. P., & Pearson, A. G. (1946). High frequency electric fields as lethal agents for insects. Journal of Economic Entomology, 39, 481-498.

TABLE 1

Comparison among replicates (Tukey test) of measured temperatures and moisture contents of wheat microwave-treated continuously or intermittently

| Treatment method | Treatment time (s) | Nominal moisture content (%) | | | | | |
|---|---|---|---|---|---|---|---|
| | | 14% | | 16% | | 18% | |
| | | F | P | F | P | F | P |
| Comparison of measured temperatures | | | | | | | |
| Continuously | 30 | 3.819 | 0.026* | 7.935 | <0.001** | 6.032 | 0.004* |
| | 60 | 0.694 | 0.503 | 2.353 | 0.102 | 1.321 | 0.273 |
| | 90 | 0.611 | 0.546 | 2.564 | 0.084 | 0.954 | 0.390 |
| Intermittently | 60 + 30 [a] | 0.398 | 0.673 | 0.091 | 0.913 | 0.128 | 0.880 |
| Comparison of measured moisture contents | | | | | | | |
| Continuously | 30 | 16.481 | <0.001** | 5.512 | 0.006* | 7.723 | <0.001** |
| | 60 | 17.770 | <0.001** | 3.710 | 0.029* | 65.751 | <0.001** |
| | 90 | 2.274 | 0.110 | 0.635 | 0.532 | 5.408 | 0.006* |
| Intermittently | 60 + 30 [a] | 0.398 | 0.673 | 0.091 | 0.913 | 0.128 | 0.880 |

[a] The first and second treatment time were 60 s and 30 s, respectively and the interruption between the first and second treatments was 5 min.

TABLE 2

Comparison (Students t-test) between measured moisture contents or temperatures of the wheat microwave-treated continuously and intermittently

| Comparison | Nominal moisture content (%) | | | | | |
|---|---|---|---|---|---|---|
| | 14% | | 16% | | 18% | |
| | F | P | F | P | F | P |
| Temperatures | −2.399 | 0.018* | −0.504 | 0.615 | −2.231 | 0.027* |
| MC | 4.097 | <0.001** | 9.792 | <0.001** | 10.108 | <0.001** |

TABLE 3

Mean, standard error (SE), maximum and minimum temperatures and moisture contents of the microwave-treated wheat under different treatment conditions

| Treat method | Nominal MC (%) | Treat time (s) | Measured temperature (° C.) [a] | | | Measured MC (%) [a] | | |
|---|---|---|---|---|---|---|---|---|
| | | | Mean ± SE | Maximum [b] | Minimum [b] | Mean ± SE | Maximum [b] | Minimum [b] |
| Con. [c] | 14 | 30 | 31.8 ± 0.4 | 40.5 (mmm) | 28.6 (ttt) | 13.9 ± 0.0 | 14.3 (mbb) | 13.5 (ttt) |
| | | 60 | 43.9 ± 1.1 | 64.2 (mmm) | 36.9 (btt) | 13.8 ± 0.0 | 14.1 (tbm) | 13.5 (ttt) |
| | | 90 | 56.1 ± 1.1 | 75.2 (bmm) | 46.8 (ttt) | 13.7 ± 0.0 | 14.1 (bmb) | 13.0 (mtt) |
| | 16 | 30 | 32.7 ± 0.5 | 38.4 (mmm) | 29.3 (ttt) | 15.8 ± 0.0 | 16.1 (tmb) | 15.5 (tbt) |
| | | 60 | 46.5 ± 1.0 | 60.7 (mmm) | 37.9 (ttt) | 15.6 ± 0.0 | 15.8 (mbm) | 15.1 (ttt) |
| | | 90 | 57.2 ± 1.4 | 77.1 (mmm) | 44.7 (ttt) | 15.6 ± 0.1 | 16.0 (mmb) | 14.6 (ttt) |
| | 18 | 30 | 32.5 ± 0.3 | 38.1 (mmm) | 29.6 (tbb) | 17.8 ± 0.0 | 18.0 (btb) | 17.6 (ttt) |
| | | 60 | 47.2 ± 0.9 | 59.4 (mmm) | 39.5 (ttt) | 17.9 ± 0.0 | 18.5 (bbb) | 17.5 (tmt) |
| | | 90 | 59.5 ± 1.6 | 75.6 (mmm) | 45.5 (ttt) | 17.9 ± 0.1 | 18.3 (bmm) | 16.9 (tmt) |
| Int. [d] | 14 | 60 + 30 [e] | 69.7 ± 1.8 | 88.4 (mmm) | 47.5 (ttb) | 13.2 ± 0.1 | 13.9 (bbb) | 12.1 (ttt) |
| | 16 | 60 + 30 [e] | 58.3 ± 1.2 | 71.9 (mtm) | 47.7 (ttt) | 15.4 ± 0.1 | 15.9 (bbb) | 14.9 (ttt) |
| | 18 | 60 + 30 [e] | 60.3 ± 1.4 | 77.8 (mmm) | 46.2 (btt) | 16.9 ± 0.1 | 17.5 (bbt) | 16.0 (tbt) |

TABLE 4

Correlation (Pearson Product Moment) between measured temperatures and moisture contents of wheat microwave-treated continuously or intermittently

| Treatment method | Nominal MC (%) | Treatment time (s) | Correlation Coefficient | P |
|---|---|---|---|---|
| Continuous | 14 | 30 | 0.147 | 0.191 |
|  |  | 60 | −0.348 | 0.001** |
|  |  | 90 | −0.306 | 0.007* |
|  | 16 | 30 | 0.023 | 0.841 |
|  |  | 60 | −0.215 | 0.050 |
|  |  | 90 | −0.257 | 0.020* |
|  | 18 | 30 | −0.269 | 0.015 |
|  |  | 60 | 0.086 | 0.447 |
|  |  | 90 | −0.330 | 0.003* |
| Intermittent[a] | 14 | 60 + 30[a] | −0.316 | 0.004* |
|  | 16 | 60 + 30[a] | −0.117 | 0.296 |
|  | 18 | 60 + 30[a] | −0.056 | 0.595 |

[a]Wheat was intermittently microwave-treated. The first and second treatment times were 60 s and 30 s, respectively with a 5 min interruption.
Significantly correlated at α <0.05* and 0.001** level.

TABLE 5

Results of A-CT (adult expelling test under continuous microwave treatment) and A-IT (adult expelling test under intermittent microwave treatment)

| Nominal MC (%) | Treatment method | Expelled adults[a] Live | Expelled adults[a] Dead | After sieving[a] Live | After sieving[a] Dead | Berlese funnel[b] Adults[a] | Berlese funnel[b] Larvae[a] |
|---|---|---|---|---|---|---|---|
| 14 | C-90[c] | 24.7 ± 1.3 | 45.3 ± 1.2 | 6.0 ± 2.0 | 24.0 ± 3.8 | 13.0 ± 2.1 | 63.0 ± 15.3 |
|  | I-90[d] | 21.0 ± 3.8 | 30.0 ± 3.2 | 10.3 ± 1.2 | 42.0 ± 2.6 | 8.0 ± 0.6 | 26.7 ± 9.4 |
|  | Control[f] |  |  | 96.7 ± 0.3 |  | 594.7 ± 153.3 | 806.7 ± 233.6 |
| 16 | C-90 | 11.3 ± 4.7 | 12.7 ± 6.5 | 11.3 ± 3.7 | 64.7 ± 2.6 | 9.0 ± 3.6 | 9.3 ± 4.6 |
|  | I-90 | 21.0 ± 4.0 | 13.7 ± 5.8 | 26.7 ± 1.2 | 38.7 ± 6.7 | 21.3 ± 7.7 | 16.7 ± 4.6 |
|  | Control |  |  | 94.3 ± 0.7 |  | 604.0 ± 51.2 | 650 ± 162.1 |
| 18 | C-90 | 16.3 ± 4.8 | 4.7 ± 1.8 | 7.0 ± 2.6 | 72.0 ± 4.0 | 11.3 ± 3.5 | 32.7 ± 21.9 |
|  | I-90 | 20.3 ± 1.2 | 11.0 ± 3.5 | 20.3 ± 2.3 | 48.3 ± 3.9 | 36.7 ± 8.5 | 108.3 ± 78.4 |
|  | Control |  |  | 84.7 ± 0.9 |  | 347.7 ± 43.7 | 263.3 ± 14.5 |

[a] The sum of expelled adults after microwave-treatment and captured adults after shaking was 100 in each replicate of all treatments. The total introduced adults were 100.
[b] Recovered insects (using Berlese funnel) after 2 mo incubation of the microwave-treated wheat.
[c] Wheat and the introduced adults were continually microwave-treated for 90 s.
[d] Wheat and the introduced adults were intermittently microwave-treated for 90 s (60 and 30 s with 5 min interruption).
[e] Wheat and the introduced adults were not microwave-treated.

TABLE 6

Results of L-CT (larvae expelling test under continuous microwave treatment)

| Nominal MC (%) | Exposure time (s) | Expelled insects[a] Larvae | Expelled insects[a] Adults | After sieving[b] Larvae | After sieving[b] Adults | Berlese funnel[c] Larvae | Berlese funnel[c] Adults |
|---|---|---|---|---|---|---|---|
| 14 | 30 | 6.7 ± 0.9 | 25.3 ± 0.9 | 19.7 ± 3.3 | 58.0 ± 1.5 | 216.7 ± 60.1 | 0.0 ± 0.0 |
|  | 60 | 7.0 ± 1.5 | 47.3 ± 3.9 | 15.3 ± 7.8 | 39.3 ± 8.7 | 1.3 ± 0.9 | 0.0 ± 0.0 |
|  | 90 | 14.0 ± 1.2 | 51.7 ± 2.9 | 18.3 ± 8.4 | 41.3 ± 5.4 | 0.0 ± 0.0 | 0.0 ± 0.0 |
|  | Control |  |  |  |  | 314.7 ± 72.9 | 97.3 ± 0.9 |
| 16 | 30 | 4.7 ± 0.9 | 13.3 ± 0.9 | 43.3 ± 5.6 | 84.3 ± 1.3 | 197.3 ± 11.9 | 0.0 ± 0.0 |
|  | 60 | 5.3 ± 0.7 | 24.3 ± 2.2 | 32.7 ± 8.4 | 56.3 ± 1.2 | 1.0 ± 1.0 | 0.0 ± 0.0 |
|  | 90 | 7.7 ± 1.5 | 29.3 ± 1.8 | 21.7 ± 2.3 | 67.0 ± 0.6 | 0.0 ± 0.0 | 0.0 ± 0.0 |
|  | Control |  |  |  |  | 354.7 ± 90.5 | 93.3 ± 0.9 |
| 18 | 30 | 4.3 ± 1.2 | 15.0 ± 1.7 | 39.7 ± 7.1 | 83.7 ± 1.8 | 485.3 ± 64.7 | 0.0 ± 0.0 |
|  | 60 | 3.3 ± 0.3 | 29.3 ± 2.7 | 37.7 ± 2.2 | 40.0 ± 4.0 | 3.3 ± 1.3 | 0.0 ± 0.0 |
|  | 90 | 6.7 ± 2.2 | 25.3 ± 4.9 | 30.0 ± 4.7 | 57.3 ± 3.8 | 0.0 ± 0.0 | 0.0 ± 0.0 |
|  | Control |  |  |  |  | 481.0 ± 103.5 | 95.3 ± 1.8 |

[a] Expelled insects after microwave-treatment.
[b] Captured insects after sieving.
[c] Recovered insects (using Berlese funnel) after 24 h of the microwave-treatment.

TABLE 7

Comparison of expelled and captured adults between continuous and intermittent treatments

|  | Expelled adults[a] | | Captured adults after shaking[a] | |
| --- | --- | --- | --- | --- |
| Nominal MC (%) | T | P | T | P |
| 14 | 6.862 | 0.002 | −6.417 | 0.003 |
| 16 | −1.594 | 0.186 | −1.594 | 0.186 |
| 18 | 1.544 | 0.197 | −1.544 | 0.197 |

[a]Comparison of sum of live and dead adults between continuous and intermittent treatments (Students t-test).

TABLE 8

Comparison (Student t-test) of expelled and captured insects among different microwave-treatment times

| Nominal MC (%) | Comparison[a] | After microwave treatment and sieving[b] | | Berlese funnel[b] | |
| --- | --- | --- | --- | --- | --- |
| | | t value | p | t value | p |
| 14 | 30 s vs 60 s | −0.126 | 0.906 | 3.538 | 0.023* |
| | 30 s vs 90 s | −1.870 | 0.135 | 3.606 | 0.023* |
| | 60 s vs 90 s | −1.212 | 0.292 | 1.512 | 0.205 |
| 16 | 30 s vs 60 s | 2.345 | 0.079 | 16.508 | <0.0001*** |
| | 30 s vs 90 s | 3.207 | 0.033* | 16.651 | <0.0001*** |
| | 60 s vs 90 s | −0.668 | 0.541 | 1.000 | 0.374 |
| 18 | 30 s vs 60 s | 4.202 | 0.014* | 7.446 | 0.002** |
| | 30 s vs 90 s | 2.778 | 0.050 | 7.499 | 0.002** |
| | 60 s vs 90 s | −2.190 | 0.094 | 2.500 | 0.067 |

[a]comparison among different microwave-treatment times, and 30 s, 60 s, and 90 s represent 30, 60, and 90 s microwave-treatment.
[b]Comparison between sums of expelled and captured adults and larvae after microwave treatment and sieving.

TABLE 8

Recovery percentage (%) of introduced *Cryptolestes ferrugineus* treated inside a microwave oven for 150 s or inside Berlese funnels for 6 h.

| | Number of introduced insects | Recovery percentage (%) or number [a] | | | | ANOVA [c] | |
| --- | --- | --- | --- | --- | --- | --- | --- |
| Stage | | MC (%) | Microwave and sieved | Berlese funnel | Control (Sieved) | N [b] | F or t | P |
| Adult | 1 | 14-16[d] | 100.0 ± 0.0A | 83.3 ± 16.7A | 100 ± 0.0A | 30 | 1.000 | 0.372 |
| Adult | 100 | 14-16[d] | 97.8 ± 0.4A | 90.6 ± 1.2B | 97.2 ± 0.5A | 3 | 25.881 | <0.001 |
| Young larvae | 1 | 14-16[d] | 83.3 ± 3.3A | 6.7 ± 3.3B | — | 30 | 16.263 | <0.001 |
| Old larvae | 1 | 14-16[d] | 83.3 ± 3.3A | 26.7 ± 8.8B | — | 30 | 6.022 | <0.001 |
| Old larvae | Unknown [a] | 14 | 103.3 ± 4.3A | 29.0 ± 9.7B | — | 3 | 6.989 | 0.002 |
| Old larvae | Unknown [a] | 16 | 104.7 ± 3.0A | 28.7 ± 6.7B | — | 3 | 10.385 | <0.001 |
| Old Larvae | Unknown [a] | 18 | 127.0 ± 10.4A | 60.7 ± 4.4B | — | 3 | 5.876 | 0.004 |

[a] For the treatments with unknown number of larvae inside the 810 cm³ wheat, it was the number of the larvae recovered. Otherwise, it was the recovery percentage.
[b] Number of replicates.
[c] When the recovery percentages of insects were compared between the two methods (Microwave and Berlese funnel methods), Students' t-test was conducted and t was provided. When the recovery percentages of insects were compared between the three methods (Control, microwave and Berlese funnel methods), ANOVA was conducted and F was provided. Different letters after the SE in each row show a significant difference between the recovery of insects (Tukey's MRT or Student's t-test).
[d]Data associated with different moisture contents were pooled because there was no significant difference among extraction percentages inside wheat with different moisture contents.

The invention claimed is:

1. A method of testing a quantity of granular material for insect infestation comprising:
    subjecting a quantity of granular material in a sealed container to sufficient microwave or radio frequency energy to heat the entire quantity of granular material to an average temperature from about 45° C. to 65° C.;
    maintaining the quantity of granular material in the sealed container at said temperature for a period of time; and
    detecting any insects exiting the granular material.

2. The method according to claim 1, wherein the period of time is at least 15 minutes.

3. The method according to claim 1, wherein the quantity of granular material is mixed during heating.

4. The method according to claim 1, wherein the average temperature is between approximately 50-60° C.

5. The method according to claim 1, wherein the average temperature is approximately 55° C.

6. The method according to claim 1, wherein the granular material is selected from the group consisting of: soil, grains, processed granular foods, and breakfast cereals.

7. The method according to claim 6, wherein the grains are selected from the group consisting of cereal grains, pulses and oilseeds.

8. The method according to claim 1, wherein the sealed container has a perforated floor.

9. The method according to claim 8, including a collector beneath the perforated floor for retaining insects passing through the perforated floor.

10. The method according to claim 8, wherein the perforations in the floor are approximately 1-3 mm in diameter.

11. The method according to claim 10, wherein the perforations are approximately 2-3 mm in diameter.

12. The method according to claim 10, wherein the perforations have an average diameter of approximately 2.7 mm.

13. The method according to claim 12, wherein the quantity of granular material is mixed by stirring.

14. A method of treating a quantity of a granular material for insect infestation comprising:
    subjecting a quantity of granular material in a sealed container to sufficient microwave or radio frequency energy to heat the entire quantity of granular material to an average temperature of between 45-65° C.;
    maintaining the quantity of granular material in the sealed container at said temperature for a period of time; and
    separating any insects exiting the granular material from the granular material.

15. The method according to claim 14, wherein the period of time is at least 15 minutes.

16. The method according to claim 14, wherein the quantity of granular material is mixed during heating.

17. The method according to claim 14, wherein the average temperature is between approximately 50-60° C.

18. The method according to claim 14, wherein the average temperature is approximately 55° C.

19. The method according to claim 14, wherein the granular material is selected from the group consisting of: soil, grains, processed granular foods, and breakfast cereals.

20. The method according to claim 19, wherein the grains are selected from the group consisting of cereal grains, pulses and oilseeds.

21. The method according to claim 14, wherein the sealed container has a perforated floor.

22. The method according to claim 21, including a collector beneath the perforated floor for retaining insects passing through the perforated floor.

23. The method according to claim 21, wherein the perforations in the floor are approximately 1-3 mm in diameter.

24. The method according to claim 23, wherein the perforations are approximately 2-3 mm in diameter.

25. The method according to claim 23, wherein the perforations have an average diameter of approximately 2.7 mm.

26. The method according to claim 25, wherein the quantity of granular material is mixed by stirring.

* * * * *